US00PP12137P2

(12) United States Plant Patent
Danziger

(10) Patent No.: US PP12,137 P2
(45) Date of Patent: Oct. 9, 2001

(54) SOLIDAGO PLANT NAMED 'DANSOSOLO'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/323,147

(22) Filed: Jun. 1, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Michelle Kizilkaya
(74) *Attorney, Agent, or Firm*—Foley & Lardner

(57) ABSTRACT

A new and distinct Solidago plant named 'Dansosolo' characterized by having small flowers; rapid growth rate and growth cycle; and flowers that are primarily arranged on the top trimester of the stem.

1 Drawing Sheet

BACKGROUND OF THE INVENTION

The present invention comprises a new and distinct cultivar of goldenrod plant, botanically known as Solidago L. and hereinafter referred to by the cultivar name 'Dansosolo'.

Goldenrods are members of the sunflower family (Asteraceae). There are approximately 100 species of Solidago plants found in North America, most of which are geographically located in the East. Goldenrods are perennial plants that commonly grow along streambanks, ditches, roadsides and other areas where the soil is moist and rich.

The new cultivar was originated from a cross made in a controlled breeding program in Mishmar Hashiva, Israel. The female parent is a Solidago cultivar designated Y-232 (unpatented). The male parent is an unknown Solidago cultivar (unpatented). 'Dansosolo' was discovered and selected by the inventor, Gabriel Danziger, as a flowering plant within the progeny of the stated cross in a controlled environment in Mishmar Hashiva, Israel.

Asexual reproduction of the new cultivar by leaf-cutting was first performed by the inventor at Mishmar Hashiva, Israel and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Dansosolo' which in combination distinguish this Solidago as a new and distinct cultivar:

1. Small flowers;

2. Rapid growth rate and growth cycle; and

3. Flowers primarily arranged on the top trimester of the stem.

'Dansosolo' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under conditions which closely approximate those generally used in commercial practice.

During the summer and in spring, the plant is grown outdoors in the soil on lifted beddings, and in winter from November to March, it is transferred to a greenhouse where it is grown in the soil on lifted beddings. The optimal temperature for growing 'Dansogold' is 15° C. to 25° C. Once it has been established, the plant can be pinched. Pinching is done at the point when the main stem has reached 5 to 10 cm, or when 2 segments are observed on the stem. Not less than a total of 16 hours of daylight is given, with additional lighting given according to the season.

Of the many commerical cultivars known to the present inventor, the most similar in comparison to 'Dansosolo' is the well-known Solidago cultivar 'Tara' (unpatented). In comparison to 'Tara', 'Dansosolo' has a similar growth habit, but the flowers of 'Dansosolo' are brighter in color and more numerous in number than flowers of 'Tara'.

BRIEF DESCRIPTION OF THE DRAWING

The accompanying photographic illustration shows a typical 'Dansosolo' plant following growth under appropriate growing conditions, with colors being as true as possible with illustrations of this type. The age of 'Dansosolo' when photographed is 3 months from the date of planting. The photographed plant grew in the soil in a greenhouse on lifted beddings.

DETAILED BOTANICAL DESCRIPTION

The following observations, measurements and values describe the new cultivar as grown in Mishmar Hashiva, Israel, under conditions which closely approximate those generally used in commercial practice. During the summer and in spring, the plant is grown outdoors in the soil on lifted beddings, and in winter from November to March, it is transferred to a greenhouse where it is grown in the soil on lifted beddings. The optimal temperature for growing 'Dansogold' is 15° C. to 25° C. The plant can be pinched once it has been established. Pinching is done at the point when the main stem has reached 5 to 10 cm, or when 2 segments are observed on the stem. Additional lighting is given according to the season and is given not less than a total of 16 hours of daylight. Color references are made to The Royal Horticultural Society Colour Chart (R.H.S.), except where general colors of ordinary significance are used. Color values were taken under daylight conditions in the morning in Mishmar Hashiva, Israel.

Origin: Mishmar Hashiva, Israel.
Parentage:
*Male parent.*—Unknown Solidago cultivar.
*Female parent.*—Solidago cultivar designated Y-232.
Classification:
*Botanical.*—Solidago L.
*Commercial.*—Goldenrod, cv. 'Dansosolo'.
Propagation: By vegetative cutting.
Plant:
*Growth habit.*—Panicle inflorescence with small yellow flowers. The main branch has many side branches with dark-green leaves.
*Height.*—70–80 cm.
*Width.*—30 cm.
*Plant vigor.*—Medium.
*Roots.*—Cutting's roots are obtained 4 weeks after rooting using a hormone to root.
Branches:
*Arrangement.*—Panicle with conical shape.
*Number.*—1–2 stems (without pinching), 5–6 stems (with pinching).
*Length.*—70–80 cm.
*Width.*—0.8–1 mm.
*Internode length.*—7–8 cm.
Foliage:
*Shape.*—Linear.
*Texture.*—Somewhat hairy leaves.
*Margin.*—Entire.
*Venation.*—One main, very thin, vein (RHS 147C).
*Color of mature leaf.*—Upper side: RHS 146A. Under side: RHS 146B.
*Color of juvenile leaf.*—Upper side: RHS 146B. Lower side: RHS 146B.
*Petioles.*—Sessile leaves.
Inflorescence:
*Capitulum.*—Form: Elongated. Type: Panicle. Diameter across face: Approximately 10–13 cm.
*Ray florets.*—Color (upper surface): Yellow (RHS 9B). Color (under surface): Yellow (RHS 9C). Shape: One row of petals. Number of rays per flower: 13. Dimension: 1–1.2 mm.
*Disc florets.*—Color (mature): Yellow (RHS 12H). Diameter of disc: Approximately 0.3 cm. Number of discs per flower: 6. Dimension: 0.5 mm.
*Number of flowers per inflorescence.*—Hundreds of flowers for each inflorescence branch; tens of flowers for a single inflorescence on the inflorescence branch.
*Natural bloom season.*—Autumn.
*Lastingness of blooms.*—10–15 days (winter), 7–10 days (summer).
*Fading.*—Flowers fade after 10–15 days (winter), 7–10 days (summer).
*Peduncles.*—Presence: Present on every flower. Length: 6 mm. Color: RHS 145A.
*Sepals.*—Not present.
*Involucore.*—Dimensions: 1 mm. Color: RHS 144C.
Reproductive organs:
*Anthers.*—Number: 6. Size: Approximately 0.5 mm. Color: Yellow RHS 5A.
*Pistils.*—Number: 6. Size: 1 mm. Color: Green RHS 149D.
*Seeds.*—0.5 mm, pappus on the edges.
*Fruit.*—Not observed.
Disease resistance: No special observations regarding sensitivity and/or resistance made.

I claim:

1. A new and distinct Solidago plant name 'Dansosolo', substantially as illustrated and described herein.

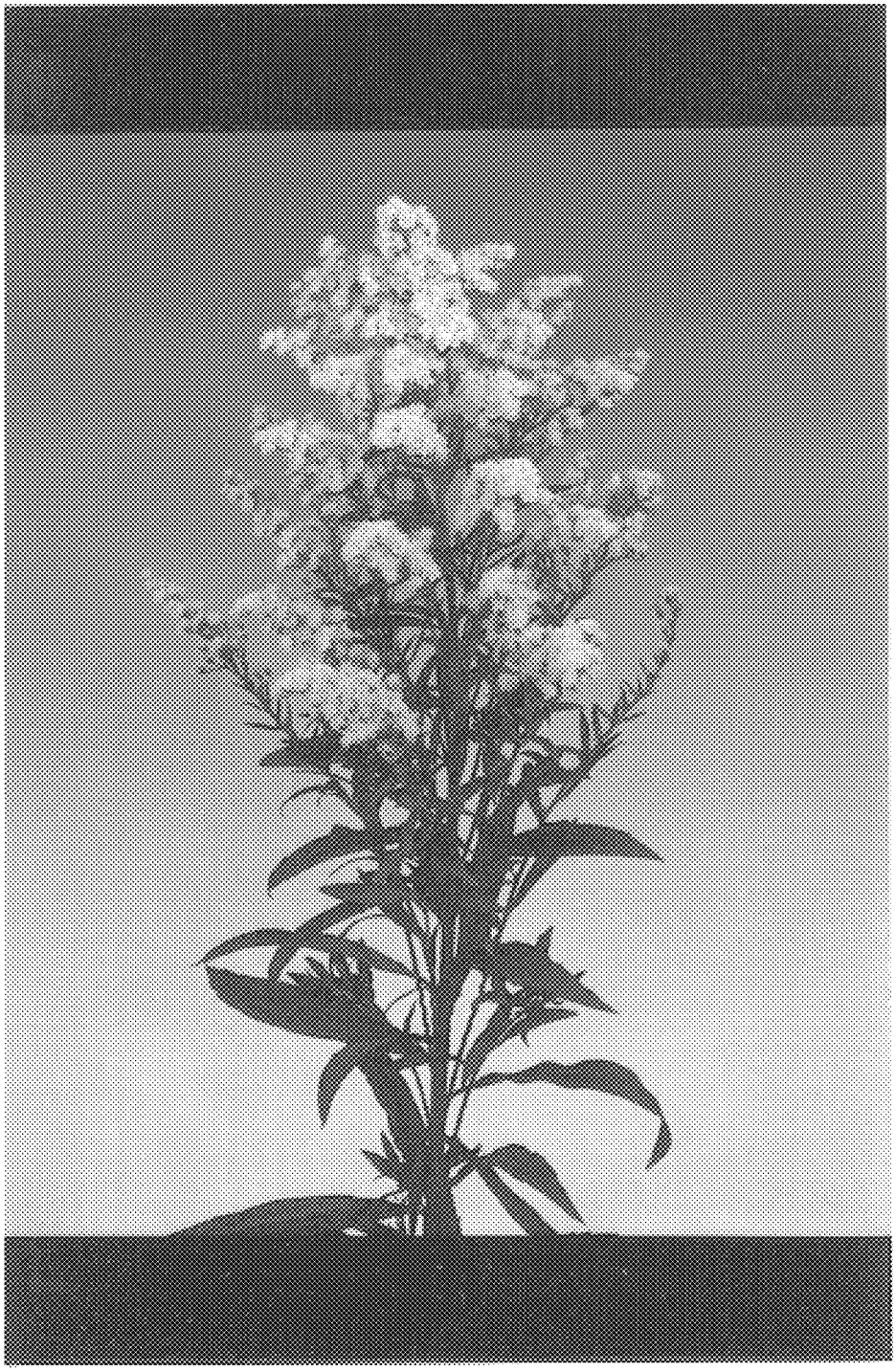

* * * * *